United States Patent [19]

Warriner

[11] Plant 5,039

[45] Apr. 12, 1983

[54] ROSE PLANT 78-5111—PETTICOAT

[75] Inventor: William A. Warriner, Tustin, Calif.

[73] Assignee: Jackson & Perkins Company, Medford, Oreg.

[21] Appl. No.: 319,106

[22] Filed: Nov. 6, 1981

[51] Int. Cl.[3] ..... A01H 5/00

[52] U.S. Cl. ..... Plt./7

[58] Field of Search ..... Plt./7

*Primary Examiner*—Robert E. Bagwill

*Attorney, Agent, or Firm*—Klarquist, Sparkman, Campbell, Leigh, Whinston & Dellett

[57] ABSTRACT

A miniature rose variety having a compact, spreading plant; an abundance of small, pink-edged white blooms with approximately 90 petals; and good mildew resistance.

1 Drawing Figure

This present invention relates to a new and distinct variety of rose plant of the miniature class which was originated by me by crossing the variety Bon Bon, U.S. Plant Pat. No. 3,555, with the variety Lemon Delight, U.S. Plant Pat. No. 4,447.

The primary objective of this breeding was to produce a new rose variety combining the vigor and plant habit of Bon Bon with the dwarf characteristic of Lemon Delight. This objective was substantially achieved along with other desirable improvements as evidenced by the following unique combination of characteristics which are outstanding in the new variety and which distinguish it from its parents as well as from all other varieties of which I am aware:

1. A compact, spreading plant reaching 30 cm. in height.
2. Abundance of small, pink edged, white blooms, having approximately 90 petals.
3. Good mildew resistance.

Asexual reproduction of this new variety by cuttings, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with The Royal Horticultural Society Colour Chart except where ordinary dictionary significance of color is indicated.

Parentage:

*Seed parent.*—Bon Bon, U.S. Plant Pat. No. 3,555.

*Pollen parent.*—Lemon Delight, U.S. Plant Pat. No. 4,447.

Classification:

*Botanical.*—Rosa hybrid.

*Commercial.*—Miniature.

FLOWER

Observations made from specimens grown at Irvine, Calif. during August.

Blooming habit: Continuous.

Bud:

*Size.*—1 cm. when petals start to unfurl.

*Form.*—Blunt top.

*Color.*—When sepals first divide, white. When half blown; upper side of petals mostly white with petal edges irregularly tinted with pink 55C; lower side of petals mostly white, with petal edges tinted pink 55C very much the same as upper side.

*Sepals.*—Color: Outer surface Green 138B, some stipitate glands on edges and surface. Three appendaged sepals lightly appendaged; two unappendaged sepals hairy edged.

*Receptacle.*—Color: Green 138B. Shape: Funnel. Size: Average. Surface: Smooth.

*Peduncle.*—Length: Short. Surface: Glandular. Color: Light green. Strength: Stiff, erect.

*Opening.*—Petals fold outward with slight recurving.

Bloom:

*Size.*—Small. Average open size is 3 to 3½ cm.

*Borne.*—In clusters, rounded.

*Stems.*—Short, strong.

*Form.*—When first open, flat. Permanence: Retains its form to the end; outer petal edges slightly curled.

*Petalage.*—Number of petals under normal conditions: 90-95.

*Color.*—Center of flower: Upper side of petals white with petal edges tinted pink 55C; reverse side of petals white with petal edges tinted pink 55C; base of petals pale yellow. General tonality from a distance, white with pink edges.

*Variegations.*—None.

*Discoloration.*—General tonality at end of first day, none; third day, petal edges sometimes darker.

*Fragrance.*—None.

Petals:

*Texture.*—Thin.

*Shape.*—Outer petals: oval, pointed. Center petals: long, narrow.

*Form.*—Tips slightly recurved.

*Arrangement.*—Imbricated. Petaloids in center, few.

*Persistence.*—Drop off cleanly.

*Lastingness.*—On the plant, very long. As cut flower, very long.

Reproductive parts:

*Anthers.*—Small, few. Color: Yellow. Arrangement: Regular around styles; mixed with petaloids; some stamens coalesced with petaloids.

*Filaments.*—Color: White.

*Pollen.*—Lemon yellow.

*Styles.*—Color: Greenish.

*Stigmas.*—Color: White.

PLANT

Form: Bush.

Growth: Vigorous, dwarf, compact, usually reaching only 30 cm. in height, spreading to 50 cm. in width.

Foliage: Number of leaflets on normal mid-stem leaves: usually 7.

*Size.*—Small.

*Quantity.*—Abundant.

*Color.*—New foliage: green. Old foliage: green.

Leaflets:

*Shape.*—Oval pointed.

*Texture.*—Upper side: leathery.

*Edge.*—Serrated.

*Serration.*—Single, small.

*Petiole.*—Rachis: Color: Green. Underside: Prickles.

*Stipules.*—Long.

*Disease resistance.*—Very resistant to mildew under normal growing conditions at Irvine, Calif.

Wood:

*New wood.*—Color: Light green. Bark: Smooth.

*Old wood.*—Color: Green. Bark: Smooth.

Prickles:

*Quantity.*—On main stalks from base, many. On laterals from stalk, many.

*Form.*—Narrow base, hooked downward.

*Color when young.*—Light green and red.

*Position.*—Irregular.

Small prickles:

*Quantity.*—On main stalks, none. On laterals, none.

I claim:

1. A new and distinct variety of rose plant of the miniature class, substantially as herein shown and described, characterized particularly as to novelty by the unique combination of its compact plant, mildew resistant foliage, pink edged white, very double flowers.

* * * * *

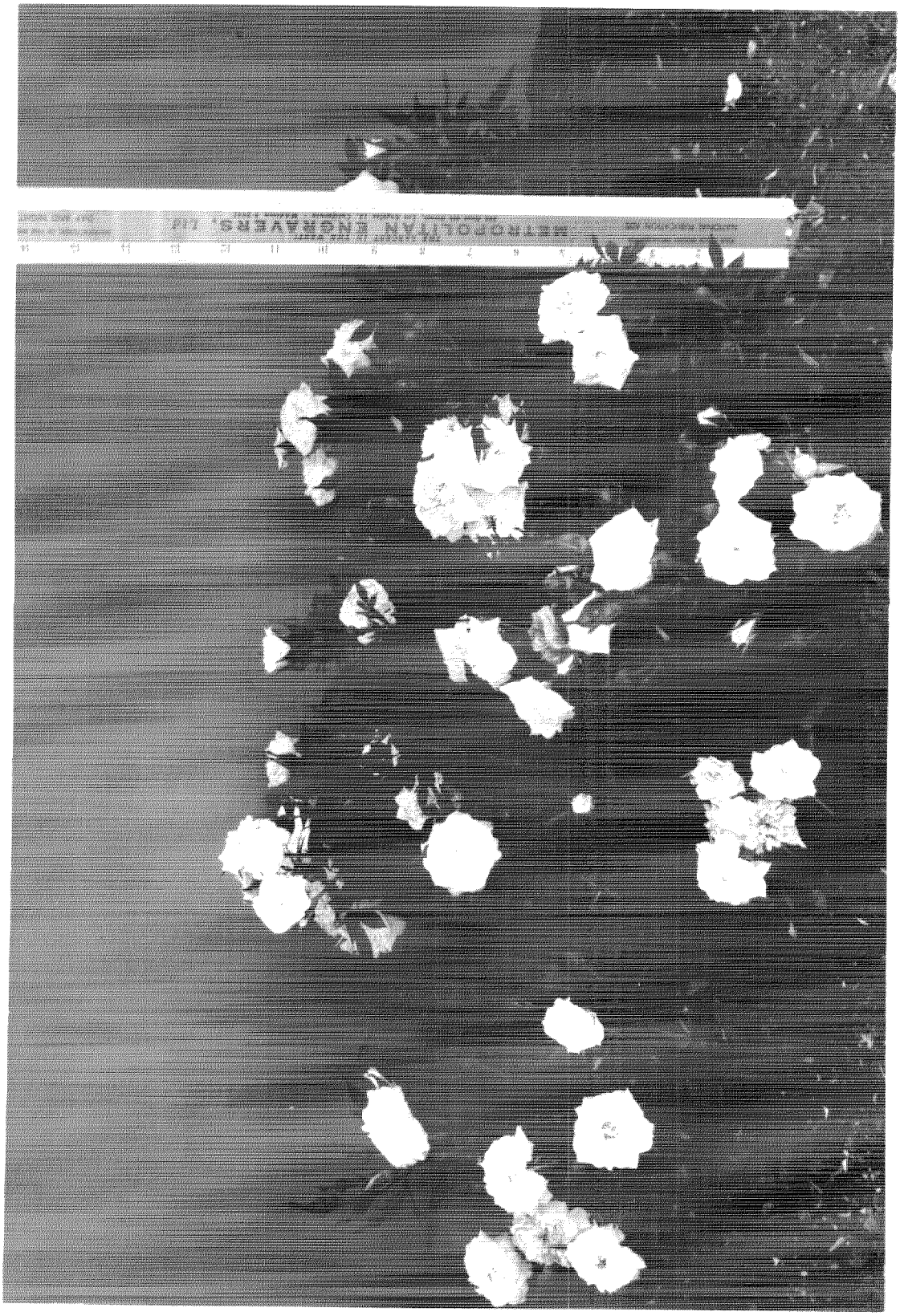
METROPOLITAN ENGRAVERS, INC.